United States Patent [19]

Boutos

[11] Patent Number: 5,571,118
[45] Date of Patent: Nov. 5, 1996

[54] APPARATUS FOR STIMULATING PENILE, SCROTAL, ANAL, VAGINAL AND CLITORAL TISSUE

[76] Inventor: David Boutos, 4420 Dunlap Crossing St., Las Vegas, Nev. 89129

[21] Appl. No.: 369,172

[22] Filed: Jan. 5, 1995

[51] Int. Cl.$^6$ ........................................................ A61N 1/05
[52] U.S. Cl. ........................................... 607/138; 607/143
[58] Field of Search .................................... 607/138, 143, 607/116; 128/644, 639; 439/8, 91

[56] References Cited

U.S. PATENT DOCUMENTS

| | | |
|---|---|---|
| 4,542,753 | 9/1985 | Brenman et al. |
| 4,564,024 | 1/1986 | Wohler, Jr. |
| 4,663,102 | 5/1987 | Brenman et al. .................... 264/222 |
| 4,742,833 | 5/1988 | Barsom . |
| 5,010,895 | 4/1991 | Maurer et al. |
| 5,385,577 | 1/1995 | Maurer et al. ........................ 607/138 |
| 5,456,709 | 10/1995 | Hamedi ................................. 607/138 |
| 5,464,448 | 11/1995 | Malewicz ............................. 607/138 |

Primary Examiner—William E. Kamm
Assistant Examiner—Scott M. Getzow
Attorney, Agent, or Firm—Meschkow & Gresham, P.L.C.

[57] ABSTRACT

Male and female electrodes for stimulating penile, scrotal, anal vaginal and clitoral tissue is shown. The electrodes are formed from elastomeric material. Electrical stimulation to such areas is intended to control incontinence, to induce penile erection where impotence occurs, or to induce excitation and orgasm. A male penile ring electrode formed from elastomeric material and intended for use in pairs, has an outer nonconductive surface, and an inner conductive portion comprising the inner surface, and the sides of the ring, and all the material between the inner surface, the sides of the ring, and the outer nonconductive surface. A contact for connecting the electrode to a source of electricity is mounted on the outer surface and connects to the inner portion. A like connector that can be used alone has two nonconductive portions separating two conductive ring sections that outer nonconductive surfaces. Female electrodes like a ball having a nonconductive ring about its centerline, and two conductive portions about said ring, and a plug having a conductive tip and sides with nonconductive material therebetween are also disclosed. Additionally anal and male urethral electrodes formed from the same material as disclosed herein are taught.

13 Claims, 4 Drawing Sheets

APPARATUS FOR STIMULATING PENILE, SCROTAL, ANAL, VAGINAL AND CLITORAL TISSUE

BACKGROUND OF THE INVENTION

1. Field of the Invention

This invention relates to apparatus for applying electrical energy to living tissue.

More particularly, the present invention relates to apparatus for electrically stimulating penile, scrotal, anal vaginal and clitoral tissue.

In a further and more specific aspects, the invention relates to electrically stimulating penile, scrotal, vaginal and clitoral tissue for the purposes of treating incontinence in men and women, and for inducing penile erection, male and female orgasm.

2. Prior Art

It is widely known that the application of electrical stimulation to certain neuromuscular areas in or near the genitalia can be used to treat incontinence in both men and women. Also known is that the application of electrical stimulation to penile tissue can cause erection where impotence may exist due to physiological or psychological conditions. Additionally it is known the application of electrical stimulation to penile, vaginal, clitoral, anal, or prostate tissue can induce orgasm, even where the subject has suffered vascular degenerative neural neuropathy. Finally it is known that diabetes and many other medical disorders can cause penile impotence.

The art is replete with various apparatus used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the vagina and the anus.

Urinary incontinence is a common problem that may require long term retraining of self-control, particularly after a stroke, or permanent use of an external control device. The prior art does not teach of apparatus that is designed to be worn while the user, fully dressed, moves about his or her everyday course of events.

Rigid rings are useable for males where the application of electrical current to only a portion of penile tissue is sufficient to induce urethral control or erection. This is because sufficient expansion room is required within the ring to accommodate penile engorgement. Rigid rings are particularly problematic where penile atrophy has occurred, and the desired goal is erection or orgasm. The tremendously varying size of the penile tissue from rest to engorgement may cause a need to use a large diameter ring on a small diameter penis, or to change rings during a treatment.

For the female, a discrete unit, usable in a variety of ways, is desirable to control incontinence, or to stimulate and to induce orgasm. Such a unit should be particularly designed to be worn under a user's clothing, and operative while the female was engaged in other normal everyday activity.

It would be highly advantageous, therefore, to remedy the foregoing and other deficiencies inherent in the prior art.

Accordingly, it is an object of the present invention to provide improvements in electrical stimulation apparatus for both men and women.

Another object of the invention is the provision of improvements especially adapted for use in connection with apparatus for controlling and treating incontinence in men and women.

And another object of the invention is to provide improved means for the application of electrical stimulation to the vagina.

Still another object of the immediate invention is the provision of an improved means for the application of electrical stimulation to the vagina, that can be easily adapted for the application of electrical stimulation to the clitoral tissue.

Yet another object of the invention is to provide means for the application of electrical stimulation to the penile and scrotal tissue.

Yet still another object of the invention is the provision of improved means for the application of electrical stimulation to the penile and scrotal tissue that can expand with penile erection.

A further object of the instant invention is to provide improvements in the connectivity of electrical stimulation apparatus.

And a further object of the invention is the provision of a male and female electrical stimulation apparatus that can be worn comfortably and discretely under a user's clothing.

Yet a further object of this invention is to provide male electrical stimulation apparatus that can induce erection and orgasm, and female electrical stimulation apparatus that can induce orgasm.

And yet an object of the invention is the provision of means and improvements according to the foregoing which will materially reduce the cost of male and female electrical stimulation apparatus.

SUMMARY OF THE INVENTION

Briefly, to achieve the desired objects of the instant invention in accordance with a preferred embodiment thereof, first provided is a female electrical stimulation apparatus having a base plate to which an electrode is attached by wire, and to which a controller may be attached. The base plate has tethers so that it may be tethered to the body of the female user.

The female electrode apparatus and its electrode are fabricated from elastomeric material. The female electrode may inserted into the vagina and positioned therein so that the application of electricity may contract the muscles surrounding the ureter, thereby controlling incontinence, or positioned therein so the application of electricity may induce excitation and orgasm. The female electrode may also be mounted in a hole in the base plate so that it may worn against the clitoral tissue, thereby also inducing excitation and orgasm.

A male electrode in the form of a ring to be wrapped around penile and/or scrotal tissue comprises an alternate embodiment of the invention. The ring is also formed from elastomeric material, and has a metal button snap contact mounted on its outside but connected electrically to the conductive material forming the sides of the ring and its interior side. In an embodiment having one electrical contact, the entire outer surface of the ring is non-conductive, and the sides of the ring and its interior side are conductive. This ring is used in pairs, where one ring is connected to the negative side of the controller, and the second ring is connected to the positive side of the controller.

An alternate male electrode ring that may be used alone has two contacts, where one contact is connected to the negative side of the controller, and the second contact is connected to the positive side of the controller. Between the contacts two small sections of the ring are non-conductive. Using the two contact ring or two of the single contact rings, electricity may be applied to the base of the penis and/or the scrotum, to thereby contract the bladder muscles to control incontinence, or positioned thereon so the application of electricity may induce excitation and orgasm.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

PREFERRED EMBODIMENT OF THE PRESENT INVENTION

Figure 1:
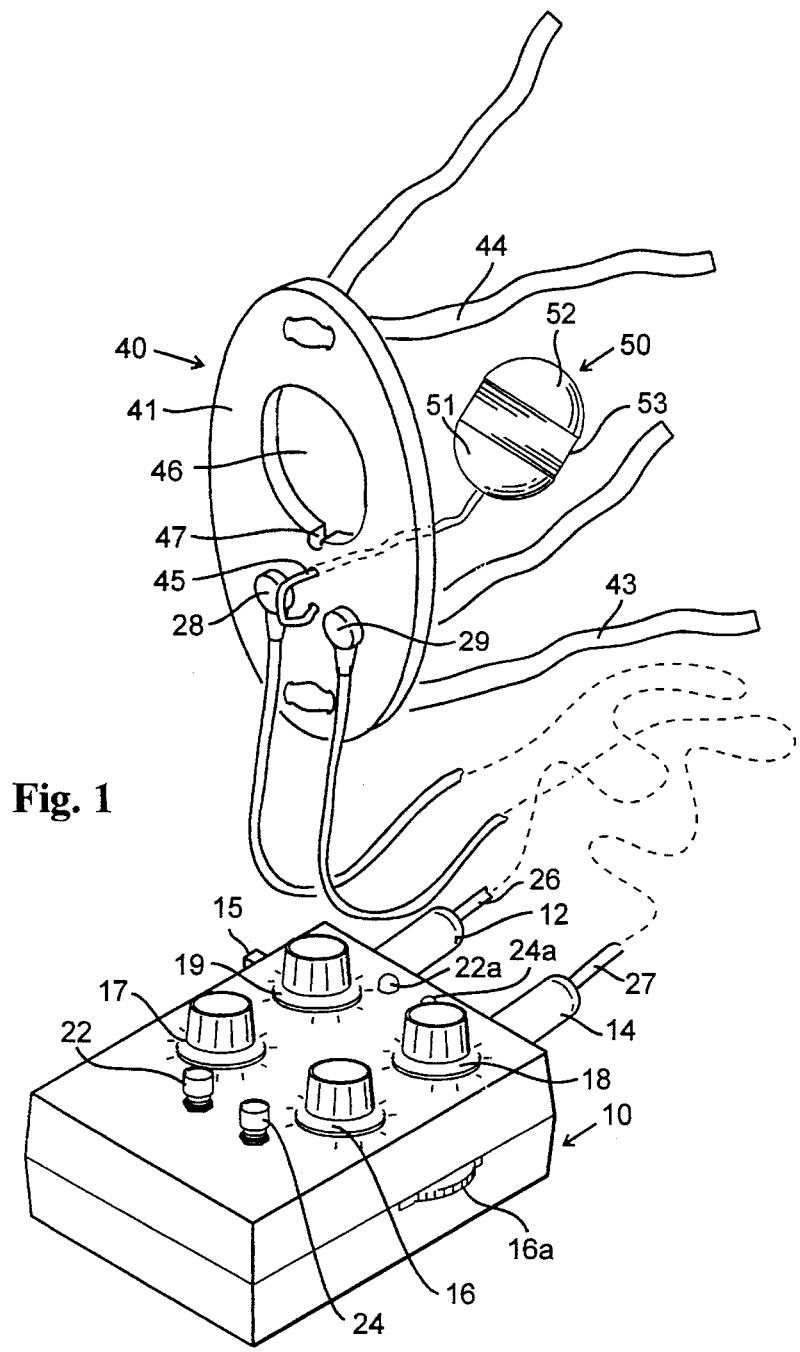
FIG. 1 is a perspective view of female electrode apparatus and controller in accordance with the present invention.

Turning now to the drawings in which like reference characters indicate corresponding elements throughout the several views, attention is first directed to FIG. 1 where controller 10 is shown. As shown herein, controller 10 has positive and negative female jacks, i.e ⅛ inch phone plugs (not shown) where wire connector plugs 12 and 14 connect to controller 10.

Controller 10 has switch 15 which selectively turns controller 10 on and off, and knobs 16, 16a, 17, 18 and 19 that modulate frequency coarse, frequency fine, pulse, power fine, and power coarse, respectively. Pushbuttons 22 and 24 can be used to kill power to either female jack on controller 10, respectively. Also included on controller 10 are lights 22a and 24a, which are lit when their respective jacks have current.

Controller 10 is generally battery powered, and generates a 9 or 12 volt DC current. This current may be modified and regulated as noted above.

Extending from plugs 12 and 14 are shielded wires 26 and 27, which terminate with button snap female contact heads 28 and 29, respectively. Inside button snap female contact heads 28 and 29, are button snap female contacts (not shown).

As shown in FIG. 1, contact heads 28 and 29 terminate at female electrode apparatus 40. Apparatus 40 has base plate 41, tethers 43 and 44, wire 45 which is connected to electrode 50, aperture 46, and wire groove 47. As will be readily apparent to one skilled in the art, the button snap female contacts in contact heads 28 and 29 are each connected to a button snap male contact. Each button snap male contact resembles contact 108 shown in FIG. 2, but in this case the two button snap male contacts are embedded in base plate 41.

Base plate 41 is fabricated from elastomeric material such as silicone, viton, and neoprene, and such material is nonconductive. The button snap male contacts embedded in it, as described above, are conductive, and are generally made from metal. Wire 45 is an insulated two strand wire, having at a first end one strand connected to one button snap male contact, and the other strand connected to the other button snap male contact. Such male connectors are embedded within base plate 41.

Electrode 50 is fabricated from elastomeric nonconductive material such as low modulus silicone, viton, and neoprene and has conductive portions 51 and 52. Electrode 50 is generally ball-shaped, e.g., spherical, oblong, or ellipitical. To make conductive portions 51 and 52 conductive, carbon particles are embedded in the silicon, viton, or neoprene. At the second end of wire 45, one strand is embedded into conductive portion 51, and the other strand is embedded into conductive portion 52. Nonconductive portion 53 insulates the circuit to conductive portion 51 from the circuit to conductive portion 52.

In general use of female electrode apparatus 40, base plate 41 is positioned over the vaginal area, generally with aperture 46 about the clitoral area. Tethers 43 and 44 are threaded through base plate 41 and may be draped around the user's body, and tied in back to hold base plate 41 in position. More on the use of female electrode apparatus 40 will be discussed in connection with FIGS. 3, and 5–7, below.

Figure 2:
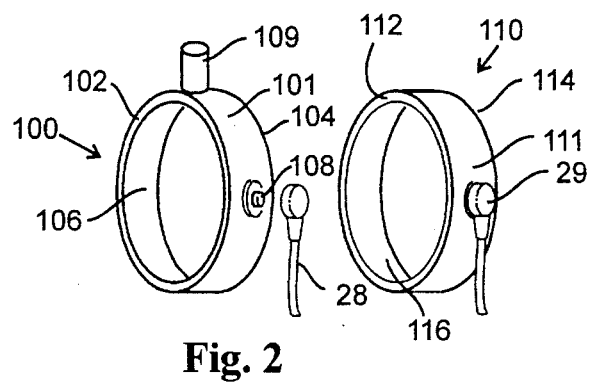
FIG. 2 is a perspective view of male electrode apparatus.

Turning to FIG. 2, shown are electrode rings 100 and 110. Rings 100 and 110 are also fabricated from elastomeric nonconductive material such as low modullus silicon, viton, and neoprene generally having a hardness of 30 shore A plus or minus 10, and elongation of 700%, and a tear strength of 50. Ring 100 has outer surface 101, side rims 102 and 104, inner surface 106, male button snap contact 108, and handle 109. Contact 108 is embedded through outer surface 101 into inner surface 106, which is contiguous with rims 102 and 104 and unshielded therebetween.

Outer surface 101 including handle 109 is nonconductive. Inner surface 106, and side rims 102 and 104 are conductive by virtue of the carbon particles are embedded in the silicon, viton, or neoprene. The carbon particles have a hardness of 65 shore A plus or minus 10, and elongation of 200%, and a tear strength of 35.

Ring 110 is structurally identical to ring 100 except ring 110 has no handle equivalent to handle 109. Ring 110 has outer surface 111, side rims 112 and 114, and inner surface 116. Handle 109 allows the user to rotate and move ring 100 forward and aft when ring 100 is in place around penile tissue, and electrical current is traveling to ring 100 from controller 10, without accidentally touching the sides 102 and 104. The same manipulation is not required for ring 110, since it is intended to placed around the top of the scrotal area.

Since each of rings 100 and 110 have one contact, they must be used in pair, or in pair with each other. These rings must be used in such pairings for the completion of an electrical circuit.

Figure 3:
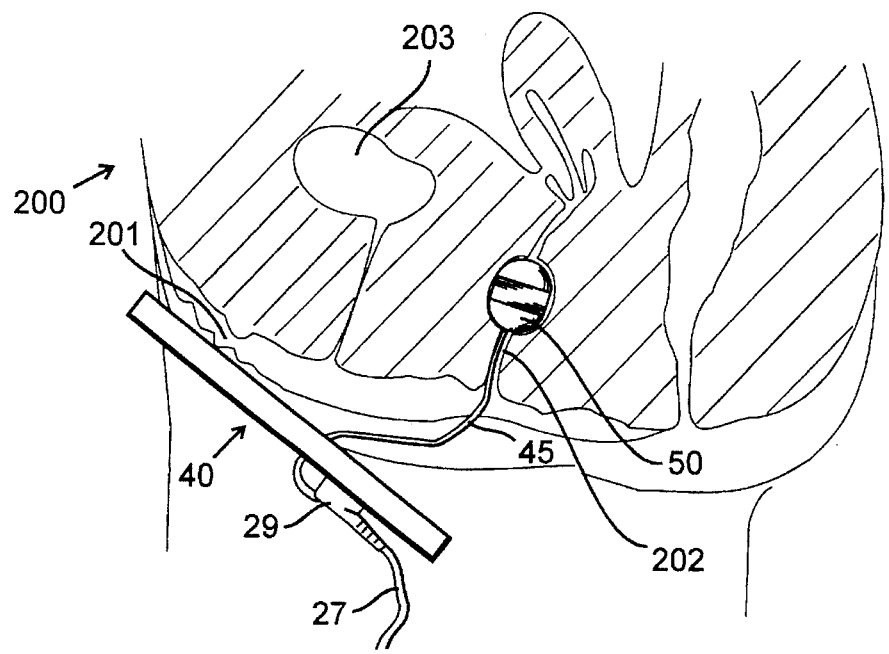
FIG. 3 is cross-sectional view of the female electrode apparatus operatively disposed within, and about the vagina of the user.

In FIG. 3 female electrode apparatus 40 is shown in place in a cross-sectional view of a female body at the lower abdomen. Shown is pelvic region 200, with clitoral area 201, vagina 202, bladder 203, and urethra 204. Wires 26 (not shown in FIG. 3) and 27 are connected to controller 10.

Female electrode in two of three modes is placed within the vagina. To control incontinence, electrode 50 is to be placed shallowly within vagina 202, and a minimal amount of electricity is applied. In this way electrical current is applied to the muscles (not shown) surrounding urethra 204 which will constrict urethra 204 thereby preventing the leakage of urine. The tethers shown in FIG. 1 may be used to hold apparatus 40 in place about the user's body, and controller 10 may be carried in a pocket.

Electrode 50 may also be placed shallowly or more deeply within vagina 202, and with adjustment of the electrical current, may be used to induce excitation and orgasm. Aperture 46 allows access to the clitoral area, if additional manual stimulation is desired.

Figure 4:
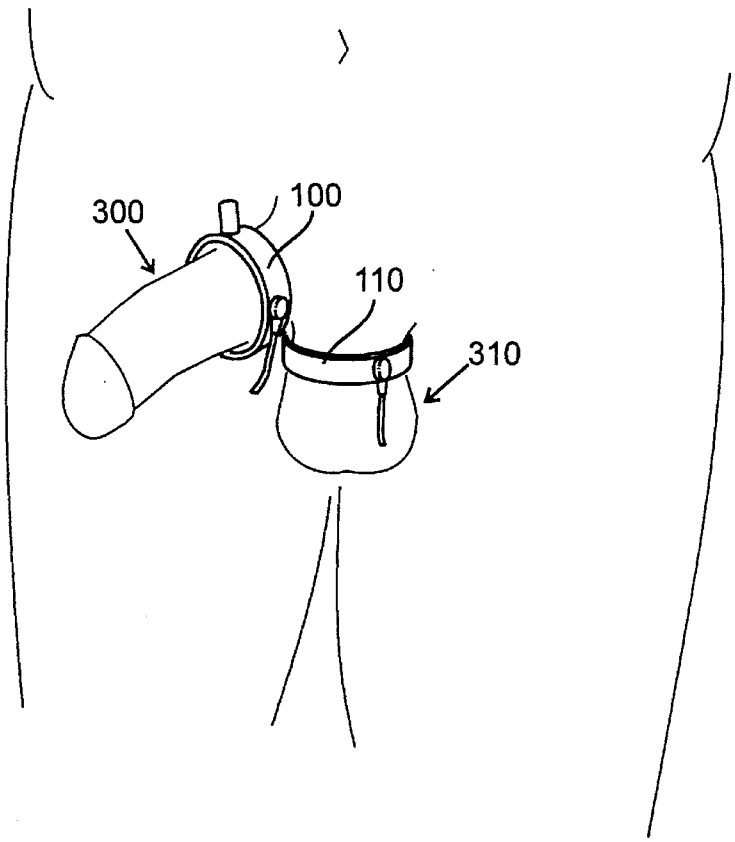
FIG. 4 is a perspective view of the male electrode apparatus operatively disposed about the penile and scrotal tissue of the user.

In FIG. 4 ring 100 is shown about the base of penis 300, and ring 110 is shown about the top of the scrotal sac. Ring 100 in particular has the ability to stretch in diameter consider, allowing a regular size ring to accommodate a normally sized penis from rest to erection, and for a small diameter to stretch considerably, as needed when used where penile atrophy or impotence has occurred.

The electrical current can be adjusted considerably with controller 10. When adjusted one way, this arrangement of rings 100 and 110 can control incontinence, and in another way can be used to induce erection, excitation and orgasm.

Figure 5:
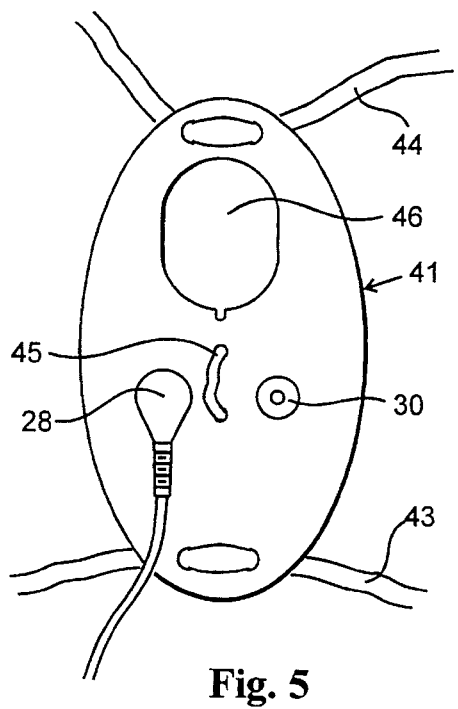
FIG. 5 is a frontal view of the female electrode apparatus.

FIG. 5 shows a frontal view of apparatus 40. Shown here is one of the male button snap contacts, contact 30. A corresponding contact rests under connector 28, while connector 28 has in it a female button snap contact.

Figure 6:
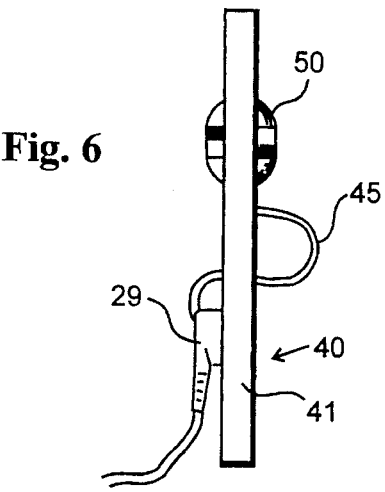
FIG. 6 is a side view showing an alternate positioning of the female electrode apparatus.

FIG. 6 shows a side view of apparatus 40, in its third and nonvaginal mode for use. In this mode, electrode 50 is placed into aperture 46, while wire 45 is tucked into groove 47. When configured in this mode, tethering apparatus 40 in position like in FIG. 3, positions electrode 50 on clitoral area 201. This mode is intended to induce orgasm with the application of electricity to the clitoris.

Figure 7:
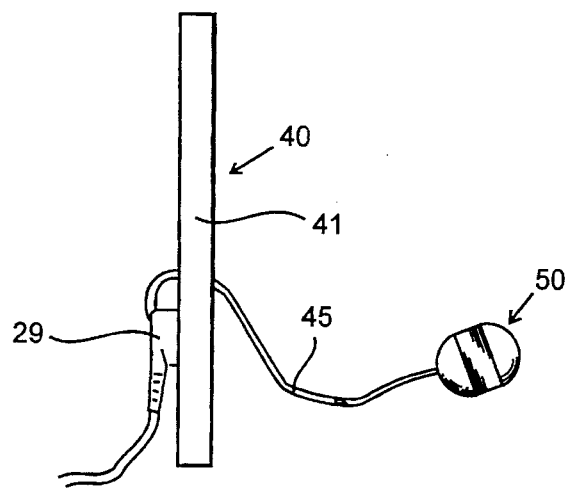
FIG. 7 is a side view showing another positioning of the female electrode apparatus.

FIG. 7 also shows a side view of apparatus 40 ready for the first two modes of use described herein. Note that to convert apparatus 40 from the mode seen in FIG. 6 to that in FIG. 7, all one has to do is to push electrode 50 from left to right (as shown in FIGS. 6 and 7) to remove it from aperture 46. Electrode 50 may also be placed within the anal cavity of a male or female for the inducement of excitation and orgasm.

The invention also encompasses an apparatus like apparatus 40 with two electrodes wired thereto (not shown). In this apparatus, each electrode is similar to electrode 50. Yet both conductive segments of each electrode is wired from one side of the two-stranded wire (analogous to wire 45), so that both electrodes must touch the body for electrical current to pass from them, and between them. Such apparatus is highly useful for stimulating bladder and ureter control muscles since the electrical current will travel through the body between the electrodes. To accomplish this, one must place one electrode at the front of the body, i.e, within the vaginal cavity, and the other at the rear of the body, i.e., within the anal cavity. A male version of this apparatus could substitute a ring like ring 100 or ring 110 for one of the ball-shaped electrodes.

Figure 8:
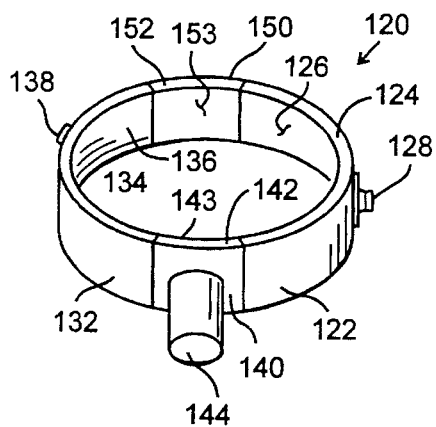
FIG. 8 is a perspective view of an alternate embodiment male electrode apparatus.
Figure 9:
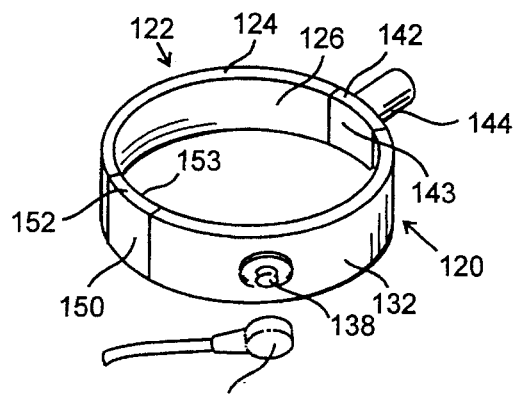
FIG. 9 is a perspective view from a different position of the alternate embodiment male electrode apparatus shown in FIG. 8.

FIGS. 8 and 9 detail alternate penile electrode ring 120. Unlike rings 100 and 110 which each have one contact and must be used in pairs, ring 120 has two contacts and may be used about the penile shaft without the use of another ring.

Ring 120 has nonconductive outer surfaces 122 and 132, and also has nonconductive portions comprising outer surfaces 140 and 150, top rims 142 and 152, bottom rims adjacent outer surfaces 140 and 150 (not shown but analogous to top rims 142 and 152), and inner surfaces 143 and 153. The inner thickness of the electrode walls between outer surfaces 140 and 150, and inner surfaces 143 and 153, respectively, are also nonconductive.

Additionally handle 144 extends from outer surface 140 and is also nonconductive, allowing ring 120 to be manually moved and rotated while electricity is applied. Such nonconductive surfaces and portions are comprised of low modullus silicon, viton, and neoprene.

Like the above electrodes, the conductive surfaces 124, 126, 134, and 136, and the bottom rims adjacent outer surfaces 122 and 132, and the inner thickness of the electrode walls between outer surfaces 122 and 132, and inner surfaces 126 and 136, respectively, are comprised of low modullus silicon, viton, and neoprene that is embedded with carbon particles. Male button snap connectors 128 and 138 are embedded through surfaces 122 and 132 into the conductive material between rims 124 and 134, and their respective bottom rims.

In use, controller 10 is connected in like fashion to electrode ring 120, as it is shown connected to female electrode apparatus 40. Snap connectors with heads 28 and 28 are connected to connectors 128 and 138.

Figure 10:
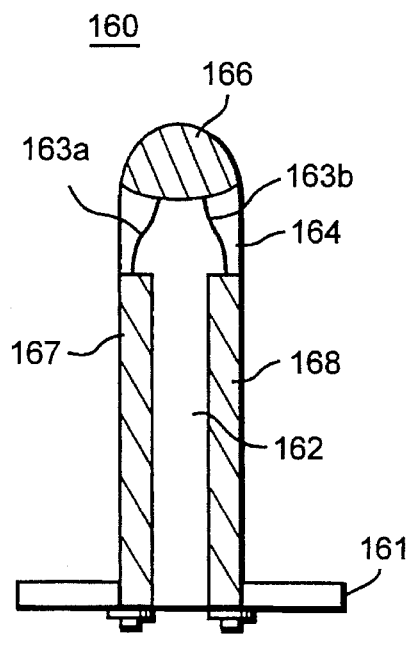
FIG. 10 is a cross-sectional view of a vaginal electrode.

Turning to FIG. 10 vaginal electrode 160 is shown. Electrode 160 is fabricated from the same materials as the other electrodes shown herein, and is nonconductive at its base and at vertical portion 162 and at portion 162. Tip 166 and side portions 167 and 168 are conductive. The tip obtains its current from the current sent to side portions 167 and 168 via wires 163a and 163b. As shown in FIG. 10, electrode 160 has two connectors, and is intended for connection like electrode 40. Base 161 is a relatively planar ellipsoid member that is also nonconductive.

It should be obvious to one skilled in the art that the conductive surfaces and portions of vaginal electrode 160 can be wired to one connector instead of two. In this way, electrode 160 can be used with another single connector electrode.

Figure 11:
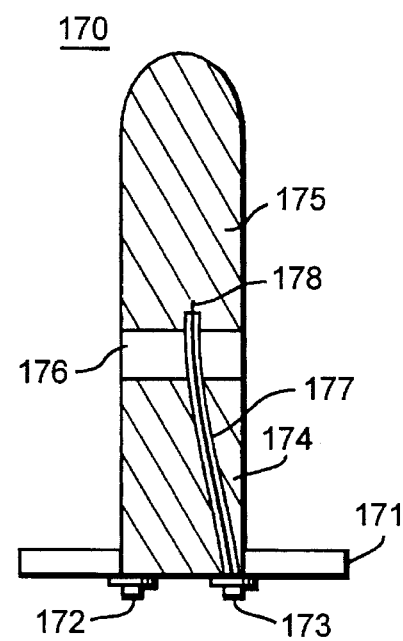
FIG. 11 is a cross-sectional view showing an alternate embodiment of the vaginal electrode shown in FIG. 10.

FIG. 11 illustrates a cross-sectional view of an alternate embodiment of a vaginal electrode formed from the same materials and in the same manner as taught herein. Electrode 170 has nonconductive base 171, through which connectors 172 and 173 are mounted. Connector 172 is mounted to be in communication with conductive portion 174, whereas connector 173 is shielded from conductive portion 174. Connector 172 will feed current to conductive portion 174. Portion 176 is nonconductive.

Shielded wire 177, which is run through conductive portion 174 as electrode 170 is formed, has a first non-shielded end connected to connector 173. Wire 177 has unshielded end 178 which feeds current to conductive portion 175. Again, it should be obvious to one skilled in the art that the two conductive portions of vaginal electrode 170 can be wired to one connector instead of two, by simply running the first unshielded portion of wire 177 connected to connector 173 into conductive portion 174. In this way, electrode 170 can be used with another single connector electrode.

Figure 12:
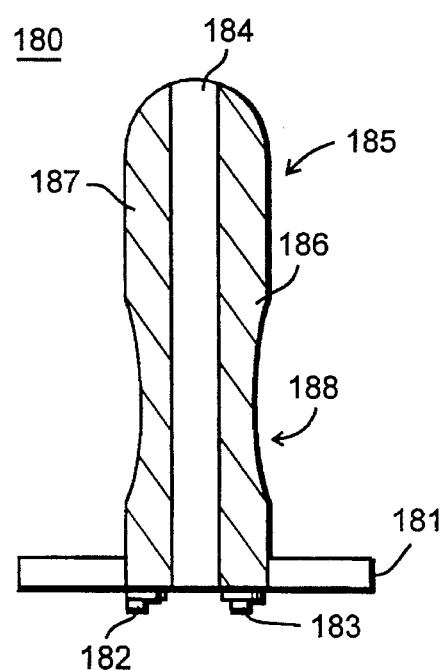
FIG. 12 is a cross-sectional view of an anal electrode.

Anal electrode 180 is formed from the same materials as taught herein and is shown in FIG. 12. It has base 181, connectors 182 and 183 mounted through base 181, nonconductive portion 184, and conductive portions 186 and 187. Anal electrode 180 has a wider portion 185, and a narrower portion 188. This allows electrode 180 to be held easily within the anal cavity when in use to control incontinence or for sexual purposes.

Figure 13:
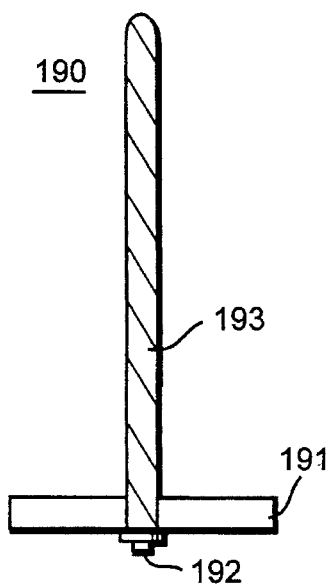
FIG. 13 is a cross-sectional view of an alternate embodiment anal electrode or a male uretal electrode.

FIG. 13 shows an electrode which can be used within the anal cavity or can be sized to fit inside the male uretal cavity. Electrode 190 which is formed from the same materials as taught herein, has nonconductive base 191, connector 192 mounted through base 191, and conductive portion 193. Electrode 190 is intended for use with another single connector electrode like ring 100.

Using electrode. 190 for uretal stimulation, while also using a single connector embodiment of electrode 180 in the anal cavity provides for an extremely efficient method of controlling male incontinence. Electrical stimulation is applied directly to the areas, as well as through the body where uretal control muscles are located. This causes them to contract thereby closing off the path to the bladder.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An electrode apparatus comprising:
   a nonconductive base;
   a plug formed from elastomeric material and having a conductive member coupled said base, said plug having a nonconductive stripe running around its circumference, and having conductive areas on both sides of said nonconductive stripe; and
   at least one electrical connector mounted to said base and in direct contact with said conductive member.

2. An electrode apparatus comprising:
   a nonconductive base;
   a plug formed from elastomeric material and having a conductive member coupled to said base, said plug having a conductive tip, a first conductive side portion, a second conductive side portion, and a nonconductive volume formed between said first and second side portions and said conductive tip, and
   at least one electrical connector mounted to said base and in direct contact with said conductive member.

3. An electrode comprising:
   a base plate which has two contacts for connecting to a source of electricity;
   two electrode means formed from elastomeric material, one of which in the shape of a ball having a conductive portion;
   a wire connected at one end to one of said contacts and connected at the other end to the conductive portion of said ball; and
   a second wire connected at one end to the other of said contacts and connected at the other end to the conductive portions of said second electrode.

4. The electrode apparatus of claim 3 wherein said second electrode is also a ball like said first electrode.

5. The electrode apparatus of claim 3 wherein said second electrode is an elastomeric conductive ring having a nonconductive outer surface.

6. An electrode apparatus comprising:
   a nonconductive base;
   a plug formed from elastomeric material and having a conductive member coupled to said base, said plug having a first conductive side portion, a second conductive side portion, a point, and a nonconductive volume formed between said first and second conductive side portions, said nonconductive volume extending to and including said point, and;
   at least one electrical connector mounted to said base and in direct contact with said conductive member.

7. An electrode apparatus comprising a ball-shaped electrode formed from elastomeric material, said ball-shaped electrode having:
   a nonconductive ring located about a centerline of said ball-shaped electrode; and
   two conductive portions separated by said nonconductive ring and located about said ring.

8. The electrode apparatus of claim 7, wherein said nonconductive ring is configured as a cylinder and each of said conductive portions is configured as a hemisphere.

9. A ring-shaped electrode apparatus formed from elastomeric material having:
   a contiguous outer nonconductive insulating surface;
   a contiguous inner conductive surface;
   a volume of conductive material between said outer and inner surfaces; and
   an electrical connector mounted on said outer surface and in communication with said inner conductive surface.

10. The electrode apparatus of claim 9, wherein said volume of conductive material terminates at two conductive side edges.

11. The electrode apparatus of claim 9 further comprising a nonconductive handle formed on said outer surface.

12. A ring-shaped electrode apparatus formed from elastomeric material, said electrode apparatus comprising:
    a first portion having a first outer nonconductive insulating surface, a first inner conductive surface, a first volume of conductive material between said first outer and first inner surfaces, and a first electrical connector mounted on said first outer surface and in communication with said first inner conductive surface;
    a second portion having a second outer nonconductive insulating surface, a second inner conductive surface, a second volume of conductive material between said second outer and second inner surfaces, and a second electrical connector mounted on said second outer surface and in communication with said second inner conductive surface;
    a first nonconductive portion joining a first end of said first portion to a first end of said second portion; and
    a second nonconductive portion joining a second end of said first portion to a second end of said second portion.

13. The electrode apparatus of claim 12 further comprising a nonconductive handle formed on one of said first and second outer nonconductive surfaces.

* * * * *